United States Patent

Rosen

Patent Number: 6,056,737
Date of Patent: May 2, 2000

[54] SKIN-MARKING DEVICES AND THEIR USE

[75] Inventor: Gerald M. Rosen, 8525 Hill Spring Dr., Lutherville, Md.

[73] Assignee: Gerald M. Rosen, Lutherville, Md.

[21] Appl. No.: 09/266,747

[22] Filed: Mar. 12, 1999

[51] Int. Cl.$^7$ .................................................. A61B 17/00
[52] U.S. Cl. ........................... 606/1; 401/23; 401/132; 606/116
[58] Field of Search ................. 606/116, 117; 401/20, 16, 196, 132; 433/229, 141; 604/3

[56] References Cited

U.S. PATENT DOCUMENTS

| | | | |
|---|---|---|---|
| 3,551,554 | 12/1970 | Herschler | 424/7 |
| 3,614,245 | 10/1971 | Schwartzman | 401/132 |
| 3,678,947 | 7/1972 | Ehrlich | 132/88.7 |
| 3,786,820 | 1/1974 | Kopfer | 132/74.5 |
| 3,802,604 | 4/1974 | Morane et al. | 222/83 |
| 4,211,323 | 7/1980 | Olsen | 206/210 |
| 4,415,288 | 11/1983 | Gordon et al. | 401/132 |
| 4,572,831 | 2/1986 | Rosen | 424/7.1 |
| 4,610,806 | 9/1986 | Rosen | 252/301 |
| 4,665,912 | 5/1987 | Burton | 128/303 |
| 4,875,602 | 10/1989 | Chickering et al. | 222/187 |
| 4,892,096 | 1/1990 | Narayanan et al. | 606/1 |
| 5,279,652 | 1/1994 | Kaufmann et al. | 106/19 |
| 5,496,304 | 3/1996 | Chasan | 606/1 |
| 5,568,988 | 10/1996 | Knox et al. | 401/40 |
| 5,743,899 | 4/1998 | Zinreich | 606/1 |
| 5,909,978 | 6/1999 | Giordano et al. | 401/188 |
| 5,927,884 | 7/1999 | Kao | 401/132 |
| 5,960,802 | 10/1999 | Sakai | 132/320 |

*Primary Examiner*—Linda C. M. Dvorak
*Assistant Examiner*—Jocelyn Debra Ram
*Attorney, Agent, or Firm*—Millen, White, Zelano & Branigan, P.C.

[57] ABSTRACT

A single use pen-like marking device is disclosed which is useful for marking skin to form marks which persist for a least a week and which are invisible under ambient light but fluoresce under ultraviolet light and to reveal cracks and caries in teeth which are difficult to see under normal light and for visualizing plaque on teeth without leaving a stain visible under normal light. It has a flexible housing with a dry wick-type marking nib in one end which communicates with the interior of the housing and which is impregnated with a skin fluorescing furanone. Inside the housing is a sealed fragile glass tube therein which contains a solvent for the furanone. The marking device is activated by bending the housing until the glass tube breaks and releases the solvent, which saturates the marking nib and dissolves the furanone therein.

7 Claims, 1 Drawing Sheet

SKIN-MARKING DEVICES AND THEIR USE

BACKGROUND OF THE INVENTION

1. Field of the Invention

This invention relates generally to a novel single use skin-marking device adapted for marking skin with marks that are visible under ultraviolet light and to a method of rendering small cracks and caries in teeth and plaque attached to teeth visible under ultraviolet light.

2. Description of the Prior Art

The use of skin marking compositions to delineate boundaries of body area requiring medical therapy or monitoring, e.g., in conjunction with radiation treatment for cancer, to mark zones for dermatological surgery, to identify areas contacted with allergens, to monitor the status of skin infections and other dermatological purposes, and to identify individual, e.g., one who have paid admission to an event, is conventional. Typically, visible compounds, such as bright purple or other brightly colored dyes or inks have been used See, for example U.S. Pat. No. 3,551,554. Although such dyes and inks are adequate for marking the skin of humans for short periods of time, e.g., a day, these visible dyes are easily removed upon washing and therefore require repeated applications for more extensive periods of skin marking as would be needed for medical purposes described above or a multiple day event. Further, the adverse psychological impact on a patient so marked with a visible dye that is visible in street clothes is significant and is impractical in most situations when an individual is to be identified by a skin mark for more than a day. In fact, in some cases, the knowledge that his or her skin would need to be marked with a visible dye that could not be immediately washed off could even result in a patient seeking an alternative therapy not requiring his or her skin being marked with a visible dye.

U.S. Pat. Nos. 4,572,831 and 4,610,806 describe the use of skin-marking compositions that contain a furanone, which reacts with the skin in about 15–30 minutes after the application thereof to form a reaction product that is invisible under ordinary invisible light but which intensely fluoresce under ultraviolet light. This reaction product resists removal by washing from the marked area for the normal lifetime of the epidermis.

As described in these patents and as shown in FIG. 1 thereof, a fluorogenically-effective concentration of a furanone, preferably fluorescamine, dissolved in an appropriate carrier fluid such as ethanol, DMF or DMSO, is introduced into the reservoir of a marking pen which is in liquid communication with a marking tip constructed of felt, porous plastic or a functional equivalent conventionally employed in the marking pen art. By drawing a line or other mark on the skin of an individual with the tip of the pen, the fluorescanine-containing carrier liquid flows through the tip of the pen and onto the skin, thereby forming along lasting mark thereon which is visible under ultraviolet light. The carrier fluid optionally also contains a coloring agent which is readily washed off the skin which renders the mark temporarily also visible under ordinary light.

Although functionally the skin marking device of these patents perform very satisfactorily, as commercial products they have a number of deficiencies. First, the half life at ambient temperature of a solution of a fluorogenically-effective amount of fluorescamine or other furanone in a dermatologically acceptable liquid is relative short, varying from days to weeks depending on the nature of the liquid, which is unacceptable for most commercial uses. Moreover, its stability is, unfortunately, the shortest in the dermatologically most desirable liquids, such as ethanol. Second, because an acceptable solvent for the furanone typically comprises a volatile organic solvent, the solvent tends to evaporate before the solution is used up, which at best alters the concentration of the furanone therein and at worst causes the solution to dry up entirely, thus reducing the number of times the marking device can be used. Third, a multiple use skin marking device which allows the tip thereof to contact the skin or other tissue of a plurality of patients can create the risk of the spread of the HIV virus or another pathological organism from an infected patient to other patients. Fourth, there is a tendency of persons involved in the skin marking procedure out of habit to treat the skin marking device of these patients in the same manner as a conventional writing instrument and as a result the marking device sometimes ends up in a pocket of a health care provider involved in a skin marking procedure and is thus unavailable for use on another patient by someone else in the same department. Therefore, a marking device which has the functional advantages of the skin-marking device of U.S. Pat. Nos. 4,572,831 and 4,610,806 but lacks the commercial deficiencies thereof would be desirable.

A problem that exists in the dental art is the detection of very small cracks and caries in teeth during a dental examination. Another problem in that dental art is that the visualization of plaque on the teeth, e.g. in conjunction with dental hygiene education, usually employs a dye which leaves a highly visible stain on the teeth which persists until the teeth are cleaned. A means of visualizing plaque without leaving such a stain also would be desirable. The skin marking procedure of the '831 and '806 patents did not seem adaptable to such usages because in the case of plaque it was not apparent that there was sufficient proteinaceous material present therein to produce a well defined fluorescing area under ultraviolet light. In the case of cracks and caries, it would seem likely that the fine line in the case of a crack and in the case of caries the circular area which would be too small to be seen by conventional visual examination would also be too small to permit contact by a solution of the furanone with the proteinaceous pulp accessible through the crack or caries and produce a fluorescing reaction product that would be visible under ultraviolet light.

OBJECTS OF THE INVENTION

It is an object of this invention to provide a single-use marking device adapted for applying a fluorogenically-effective amount of a furanone such as fluorescamine to the skin or other proteinaceous material to provide a mark thereon which is visible under ultraviolet light and which resists removal by washing. Another object is the provision of a method of rendering small cracks and caries in teeth readily visible under ultraviolet light. A further object is the provision of a method of rendering plaque on the teeth of dental patients visible without leaving a stain on the teeth which is visible by ambient light. Other objects will be apparent to those skilled in the art to which the marking device and to which these methods pertain.

SUMMARY OF THE INVENTION

In an article of manufacture aspect, this invention relates to a single use disposable pen-like marking device adapted for manually marking the skin or other proteinaceous surface with a mark which fluoresces under ultraviolet light, which comprises (a) an elongate a hollow housing having a closed end, an open end and a manually distortable flexible sidewall; (b) a dry wick marking nib fitted in the open end of the housing, one end of which projects into and is in fluid communication with the interior of the housing and is impregnated with an amount of a skin ultraviolet fluorescing furanone sufficient for a single use of the marking device; (c) a sealed frangible glass or plastic solvent tube fitted in the interior of the housing, which exterior dimensions relative to the interior dimension of the housing is such that the tube can be cracked or broken and the liquid contents thereof released into the interior of the housing by bending or squeezing the sidewall of the housing; and (d) a volume of a dermatogically acceptable solvent for the furanone in the sealed solvent tube sufficient when the tube is broken to dissolve the furanone in the wick in the solvent released from the tube and saturate the wick marking nib with the resulting solution, thereby permitting the transfer of the resulting solution of the furanone in the solvent to a surface to be fluorescently marked by the furanone.

In a method aspect, this invention relates to a method of visualizing a small crack or cavity in a tooth which comprises the steps, prior to the dental examination of teeth to be examined for cracks and caries, of (a) applying to the teeth a solution in an orally physiologically acceptable liquid solvent therefor of an amount of a skin fluorescing furanone effective to cause a crack or caries in a tooth to become visible by fluorescing under ultraviolet light; (b) waiting until the furanone has reacted with any proteinaceous material exposed by a crack or caries in a tooth; and (c) thereafter examining the teeth under ultraviolet light for an area of a tooth which fluoresces due to the presence of a crack or caries in the surface thereof.

In a second method aspect, this invention relates to a method of visualizing the plaque on natural teeth which comprises the steps, after self-cleaning of the teeth or prior to their being cleaned by a dentist or dental hygienist, of (a) applying to the teeth a solution in an orally physiologically acceptable liquid solvent therefor of an amount of a skin fluorescing furanone effective to cause plaque on a tooth to become visible by fluorescing under ultraviolet light; (b) waiting until the furanone has reacted with any plaque on a tooth to which the solution was applied; and (c) thereafter examining the teeth under ultraviolet light for an area of a tooth which fluoresces due to the presence of plaque on the surface thereof.

BRIEF DESCRIPTION OF THE DRAWINGS

With reference to the drawings, which show a preferred embodiment of this invention.

DETAILED DESCRIPTION OF THE INVENTION

Figure 1:
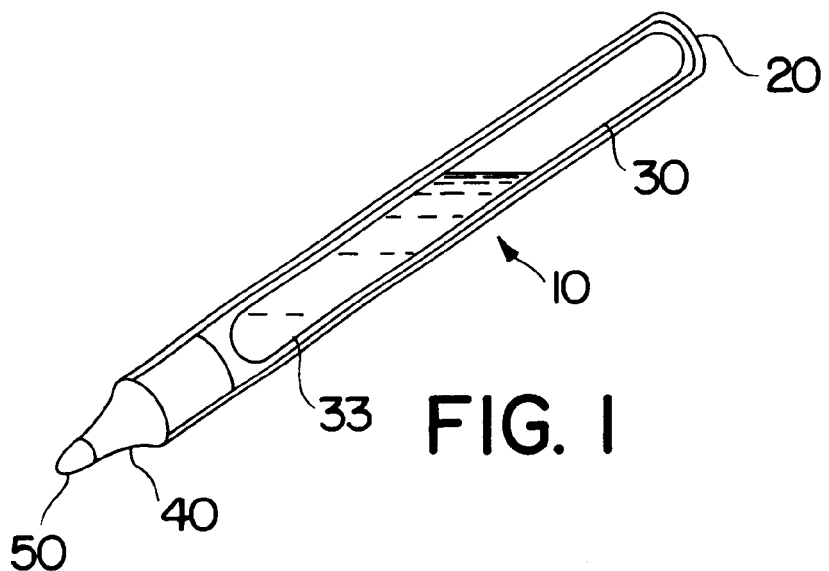
FIG. 1 is a side view of a marking device of this invention prior to being activated by the release of the solvent therein from the sealed tube containing it.

The preferred embodiment of the marking device of this invention consists of four parts or elements shown separately in FIGS. 2–5, which, when assembled as shown in FIG. 1, form a marking device 10 suitable for marking skin or proteinaceous surface so that it fluoresces under ultraviolet light. The housing, solvent tube, cap and nib elements are the same structurally as those of a commercially available marking device. The marking device of this invention differs therefrom by the chemical employed as the marking compound and by being impregnated in the nib element rather than dissolved in the carrier liquid in the solvent tube.

Figure 2:
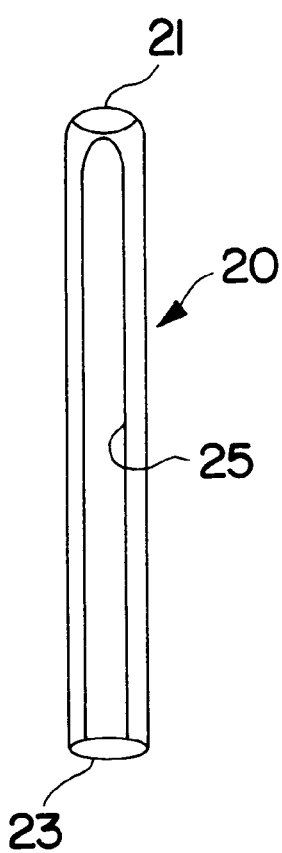
FIG. 2 is a cross-sectional side view of the tubular shaped housing element of the marking device of FIG. 1.

The housing 20 element thereof shown in FIG. 2 is a flexible walled plastic tube which is closed at one end 21 and open at its other end 23 and whose side wall 25 is flexible and can be readily compressed or bent manually. Its dimensions typically are 2–6 inches in length and 0.2–0.4 inches in diameter and its wall thickness typically is from 0.02–0.06 inches, depending upon the flexibility of the plastic from which it is formed.

Figure 3:
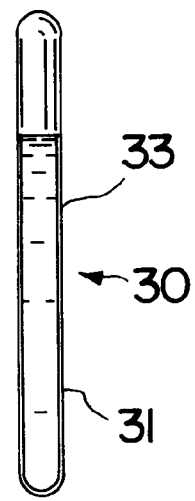
FIG. 3 is a perspective side view of the solvent tube element of the marking device of FIG. 1.

The solvent tube 30 element thereof shown in FIG. 3 is a thin-walled glass or frangible glass or plastic cylindrical vial which is sealed at both its ends and is shorter than housing 20 so that a cap 40 described hereinafter can be fitted into the open end 23 of housing 20. Its side wall 31, which typically is about 0.010 to 0.015 inches thick, is fragile and can readily be broken manually by being bent or compressed. Contained within solvent tube 30 is a volatile solvent 33 for the furanone described hereinafter. The solvent is dermatologically acceptable when the marking device is used to mark skin and is orally physiologically acceptable when the marking device is used to mark teeth. It optionally can contain dissolved therein a conventional washable dyestuff or pigment for temporarily rendering the marks formed with the marking device visible in ambient light.

Figure 4:
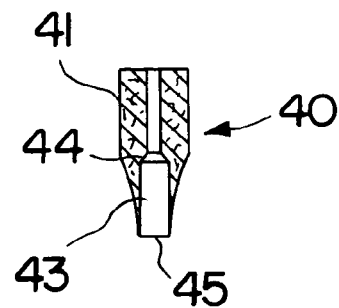
FIG. 4 is a cross-sectional side view of the cap element of the marking device of FIG. 1.

The cap 40 element thereof shown in FIG. 4 has a thicker end portion 41 which is adapted to fit tightly in open end 23 of housing 20 and is sufficiently resilient to permit it to be firmly seated within housing 20 without cracking or deforming the side wall of housing 20. Cap 40 has a thinner distal end 43 joined to thicker end 41 by an annular ledge 44 which forms a stop which determines the depth to which thinner distal end of cap 40 can be inserted into housing 20, and thus acts as an O-ring gasket for the open end of housing 20. The distal end 43 of cap 40 is thinner than the thicker end portion 41 and the diameter of the portion of core 45 therein is smaller than the portion thereof in open end 23.

Figure 5:
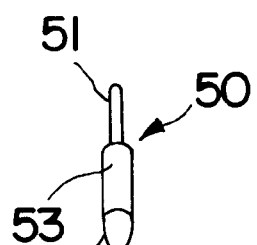
FIG. 5 is a side view of the marking nib element of the marking device of FIG. 1.

The marking nib 50 element thereof shown in FIG. 5 is formed of a porous inert material, such as polyester, polyvinylidene fluoride or cellulose fibers or open celled flexible foamed polyurethane or polystyrene, which enables the nib to act as a wick for adsorbing and transporting the solvent released from tube 30 when its side wall 31 is fractured or crushed by sidewall 25 of housing 20 being compressed or bent. Nib 50 has a thinner end portion 51, whose external diameter is about the same as or slightly less than the diameter of hollow core 45 of cap 40 and thus can be snugly fitted into cap 40 with the distal end of that thinner end portion extending to the same distance as cap 40 into interior of housing 20, and a wider end portion 53 whose external diameter is larger than the internal diameter of open portion 23 of housing 20 and thus acts as a stop which determines how far into hollow core 45 of cap 40 nib 50 can be inserted. The distal end of wider end portion 53 of nib 50 is shaped to form a marking tip 55, which has a configuration, e.g., wedge shape, so that either a thin or thick line of the solution of furanone in the solvent which is impregnated in tip 55 can be drawn with tip 55 on skin or other tissue or conical or dome shaped, so that a spot of the solution of the furanone can be applied precisely to a surface of a tooth to be examined for cracks, caries or plaque. At least the thinner proximate end 51 and preferably all of nib 50 is impregnated with a furanone which forms a reaction product with the protein of skin or present in the plaque which forms on teeth or in the pulp which is exposed when a crack or cavity forms on the surface of a tooth.

In another embodiment (not shown), at least the internal diameter of housing 20 narrows from a distance from its open end 23 corresponding to or slightly longer than the length of thinner end portion 51 of nib 50 so that the latter can be fitted therein and thus provide the function of cap 40 and eliminate the need therefor.

Before the marking device 10 is assembled, at least the thinner portion 51 of nib 50 and preferably all of nib 50 is impregnated with a volume of a solution of the furanone in a volatile solvent, e.g., acetone, tetrahydrofuran or a mixture thereof, which will impregnate nib 50, when tube 30 is broken, with an amount of the furanone effective to produce the desired fluorescing mark or marks on the selected area of skin or other surface. The volatile solvent is then removed from nib 50 by air drying or evaporation under a vacuum until nib 50 is dry. Nib 50 can then be stored in a dry atmosphere until it is assembled into a marking device 10.

To assemble the elements 20, 30, 40 and 50 into a marking device, a sealed tube 30 containing solvent 33 is inserted into housing 20 and the thicker end portion 41 of a cap 40 is fitted into the open end 23 of housing 20. The thin end portion 51 of nib 50 impregnated with the selected furanone is then inserted into the hollow core 45 of cap 40, thereby sealing housing 20. The assembled marking device can then be sterile sealed within a moisture impervious package (not shown) to protect the furanone from decomposition during storage and maintain sterility.

To use the marking device 10, the sidewall thereof is compressed manually sufficiently to cause thin wall 31 of sealed tube 30 to break, thereby releasing solvent 33 therefrom, which then flows to end 51 of nib 50 and then by wicking action to the center portion 53 thereof and finally, when nib 50 becomes saturated with the solvent, to the distal marking tip 55 thereof, thereby allowing the solvent to dissolve the furanone in nib 50 and saturate the marking tip and enable it to transfer the furanone to the surface to be fluorescently marked. When the surface is skin, the furanone reacts with the protein therein. When the surface is a tooth, the solvent seeps through any crack or caries therein and the furanone reacts with the pulp therein and any plaque thereon, thereby permitting the reaction product to be visualized with an ultraviolet light about 5 minutes to a twenty minutes thereafter.

In its method of use, this invention relates to: (a) the delineation of cracks or caries by marking the pulp below the surface of the crown of the tooth, and (b) the binding to plague as an assessment of the quality of dental care and similarly related uses for temporarily identifying a defined area so marked. The marked regions are identifiable under ultraviolet light for a prolonged period of time.

The marking device and methods of this invention employ as a transporting vehicle to transport the furanone used to fluorescently mark the desired surface a non-toxic solvent which is dermatologically acceptable when use to mark skin and is orally physiologically acceptable when used to delineate cracks or caries in teeth or to bind to plaque. Generally speaking, because only a small amount thereof is employed, almost any volatile solvent, both water soluble and water insoluble, may be used. Preferred, however, are solvents which are commonly employed for other dermatological or dental purposes, e.g., acetone, ethanol, mineral spirits and mixtures thereof, both anhydrous and aqueous.

The skin marking furanone present in the nib of the marking devices of this invention is a furanone of the formula

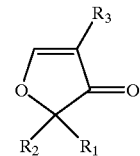

where $R_1$ is lower alkoxy or phenyl lower alkoxy and $R_2$ is

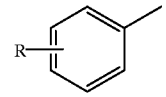

or, $R_1$ and $R_2$ collectively are

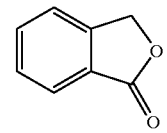

where R in each instance is hydrogen or one or more of halogen, lower alkyl, trifluoromethyl, lower alkoxy, nitro, cyano, carboxy or carboxy lower alkyl, and $R_3$ is lower alkyl, phenyl lower alkyl or aryl, in the nib in which the furanone compound is stable. Particularly preferred compounds are those wherein $R_1$ and $R_2$ are 2-coumaranone and $R_3$ is phenyl, such as 4-phenylspiro[furan-2(3H),1-phthalan]-3,3'-done.

The fluorogenic compounds employed in the composition of this invention are:

(a) non-toxic, that is, substantially free from any significant toxic effects at their effective applied concentration;

(b) substantially free of side-effects detected to the person treated;

(c) visible after being applied to teeth, plaque or other tissue only under ultraviolet light and invisible under ordinary white light; and (d) long lasting, that is, once applied they can be observed without frequent reapplications.

As used herein, the term "fluorogenic" means that a compound will produce highly fluorescent substances upon reaction with primary or secondary amine-containing biomolecules to form covalent bonds. An example of such a reagent is fluorescamine (4-phenylspiro[furan-2(3H),1-phthalan]-3,3'-dione). This furanone and others, and their preparations are disclosed in U.S. Pat. Nos. 4,045,487; 3,830,629; 3,871,825; 3,969,373; 4,045,487 and 4,238,589. Their use as disclosed in those patents is explicitly directed only to in vitro detection of proteins in laboratory solutions, labeling of exposed protein cell-surface markers and in vitro labeling of surface proteins of functional absorptive surfaces such as that of tapeworms.

In an article of manufacturing aspect, this invention relates to a method for the delineation of cracks in teeth by marking the pulp below the surface of the crown of the tooth, and the binding to plague as an assessment of the quality of dental care and similarly related uses for temporarily identifying a defined area so marked. Surprisingly, the marking reagents employed in the marking device and the methods of this invention can access and selectively and covalently bind to amino groups of cellular or extracellular tails of proteins of the pulp of teeth which are exposed to the surface of a tooth by a small crack or caries therein and fluoresce under ultraviolet light so that a crack or caries too small to be readily detected visually in normal ambient light becomes readily visible under ultraviolet light.

The solvent for the fluorogenic compound assists in transporting it to the primary or secondary amine-containing biomolecules to form covalent bonds. Examples of such carrier fluids include simple organic solvents such ethanol, isopropanol, acetone, ethyl acetate, dimethylformamide, dimethylsulfoxide and mixtures thereof. The preferred carrier fluids will be dermatologically acceptable so as to avoid unwanted irritation or other untoward toxicity due to the carrier fluid. Because it is the carrier fluid's physical ability to carry a fluorogenic reagent localized in the nib that is necessary to this invention, rather than a particular type or chemical structure of the fluids, it is apparent that many different types or mixtures of such carrier fluids are equivalent to those specifically distinguished. Thus, the viscosity of the carrier fluid may vary widely although the viscosity must allow the transport of the fluorogenic compound through the capillaries of the nib onto the surface of the tissue to be marked. Fluid of varying degrees of penetrating ability may be selected as appropriate for the particular type of tissue and/or medical application.

Because it is the ability of the furanone to penetrate cracked teeth, plaque or other tissues and its fluorogenic ability to become fluorescent after covalently bonding to amine groups that is necessary to this invention, it is apparent that other reagents will be equivalent to those specifically distinguished in this disclosure. Because it is fluorogenic product-producing ability rather than an exact chemical structure of the furanone which is critical to this invention, it will be apparent to those skilled in the art that other fluorogenic-producing reagents can meet the criteria listed herein above.

When the four components are assembled, as shown in FIG. 1, the single-delivery marking device is ready for use. Upon pressing the plastic tube between a person's fingers, the glass ampoule is broken, releasing a volume (e.g., 0.25 mL) of a dermatologically acceptable carrier fluid to wet the nib. Sealed cap is selected so that when pressure is applied by the fingers to the side wall of the plastic tube, the carrier fluid only wets the nib and does not leak directly from the plastic tube. The wet nib permits a sufficient volume of a furanone-containing carrier fluid to be transferred to the pulp of the teeth or plaque on the teeth to render it visible under ultraviolet light after the furanone reacts therewith.

The single use marker of this invention eliminates the fear of infection from HIV, which directly affects the patient, the technician applying the furanone-containing carrier fluid to the patient and the physician or dentist examining the patient. Also, in clinical uses where the physician and dentist come in contact with the blood of the patient, a single use making system is necessary to protect health care providers from infections carried by the patient.

PREPARATION AND USE

The composition of this invention can be prepared by dissolving a furanone compound as defined above in an appropriate volatile carrier fluid, which rapidly evaporates at room temperature. For example, dissolve 10 to 20 mg, preferably 15 mg of such a furanone, preferably fluorescamine, in 1 mL of the selected volatile carrier fluid, preferably acetone.

The marking composition can be introduced into the nib by placing the nib into the acetone solution containing fluorescamine. The nib will absorb about 0.15 mL of the acetone solution. Drying the wet nib in a fumed hood, which takes about 5 minutes, allows the acetone to evaporate.

From the foregoing description, one skilled in the art can easily ascertain the essential characteristics of this invention, and without departing from the spirit and scope thereof, can make various changes and modifications of the invention to adapt it to various usuages and conditions. The entire disclosures of all applications, patents and publications, cited above and below are incorporated by reference. The following preferred specific embodiments are, therefore, to be construed as merely illustrative and not limitative of the disclosure in anyway whatsoever.

EXAMPLE 1

To prepare a marking device according to this invention to use for indicating an area of skin for radiation therapy, dissolve 15 mg of fluorescamine in 1 mL of acetone. Place a nib 50 (narrow end 51, 0.5 inches in length and 0.125 inches in diameter; marking tip 55, 0.25 inches in length and 0.187 inches in diameter; formed of high density polyethylene), into this solution, absorbing 0.15 mL of the acetone solution of fluorescamine. Dry nib 50 by evaporation, leaving the nib impregnated with the fluorescamine. Partial fill an open ended 1 mL glass ampoule corresponding to tube 30 with 0.25 mL of isopropanol, seal and insert through its open end 23 into a flexible housing 20 formed of flexible polyvinyl chloride (0.31 incheas in diameter, wall thickness 0.04 inches). Insert dried nib 50 into core 45 of the narrow end 43 projecting from the open end 23 of housing 20, thereby producing a marking device as shown in FIG. 1.

EXAMPLE 2

A skin-marking composition is prepared by stirring 20 mg of 4-phenylspiro[furan-2(3H),1-phthalan]-3,3'-dione in 1 mL of tetrahydrofuran. Dip a nib 50 into this solution until it absorbs 0.15 mL of the tetrahydrofuran solution. After evaporation, the nib impregnated with 4-phenylspiro[furan-2(3H),1-phthalan]-3,3'-dione is fitted into a cap 40 fitted into a flexible polypropylene housing 20 of the skin marking pen 10 which contains a sealed glass ampoule 30 containing 0.25 mL of 95% ethanol, as shown in FIG. 1.

EXAMPLE 3

Follow the procedure of Example 1, employing 0.25 mL of dimethylsulfoxide or dimethylformamide.

EXAMPLE 4

Follow the procedure of Example 1,2, or 3 but employ a carrier fluid 33 containing dissolved therein a non-reactive fugitive dyestuff or pigment, e.g. 0.05 mL of conventional washable blue dye, thereby producing a skin marking device which produces a mark on skin that is visible under ordinary light until the skin is washed and after 15–30 minutes, which is visible under ultraviolet light for 1 week, even after repeated washing of the skin.

EXAMPLE 5

Employing a marking device 10 produced according to the procedure of Example 1,2,3, or 4, mark the skin of cancer patients to indicate sites where skin lesions were removed by surgery so if additional surgery is required after pathological evaluation of the removed tumor the site of the original tumor can be defined, or to mark areas of skin to which allergens are to be applied for allergy diagnostic purposes.

EXAMPLE 6

Employing a marking device 10 produced according to the procedure of Example 1,2,3, or 4, mark the periphery of a skin lesion to monitor progressive changes in size and shape by marking a line around its circumference.

EXAMPLE 7

Employing a marking device 10 produced according to the procedure of Example 1,2 or 3, identify cracks and caries in teeth, which are difficult to detect under normal light by painting the tooth or teeth being examined marking it with the nib saturated with a solution of fluorescamine in an orally physiologically acceptable carrier fluid (e.g., 70% ethanol). Only the pulp and not the calcified crown of the tooth will react with the fluorescamine, resulting in fluorescence after about 15 minutes which can be seen under ultraviolet light. This allows the dentist to determine whether there is a cracked tooth and caries therein and the extent of the crack or caries.

EXAMPLE 8

Employing a marking device 10 produced according to the procedure of Example 1,2 or 3, locate and define the extent of plaque attachment to teeth by marking the area of interest with its marking tip 55 saturated with an orally pharmacologically acceptable solvent containing fluorescamine. Only the plaque and not the calcified crown of the tooth reacts with fluorescamine, resulting after about 15 minutes in fluorescence which can be seen under ultraviolet light. This allows the dentist to not only determine the extent of plaque formation, but to visually show the patient the degree of the plaque adherence to the teeth and develop a strategy for future dental to minimize plaque deposits.

What is claimed is:

1. A single use disposable pen-like marking device adapted for manually marking the skin or other proteinaceous surface with a mark which fluoresces under ultraviolet light, which comprises (a) an elongate a hollow housing having a closed end, an open end and a manually distortable flexible sidewall; (b) a dry wick marking nib fitted in the open end of the housing, one end of which projects into and is in fluid communication with the interior of the housing and is impregnated with an amount of a skin ultraviolet fluorescing furanone sufficient for a single use of the marking device; (c) a sealed frangible glass or plastic solvent tube fitted in the interior of the housing, whose exterior dimension relative to the interior dimension of the housing is such that the tube can be cracked or broken and the liquid contents thereof released into the interior of the housing by bending or squeezing the sidewall of the housing; and (d) a volume of a dermatologically acceptable solvent for the furnanone in the sealed solvent tube sufficient when the tube is broken to dissolve the furanone in the wick in the solvent released from the tube and saturate the wick marking nib with the resulting solution, thereby permitting the transfer of the resulting solution of the furanone in the solvent to a surface to be fluorescently marked by the furanone.

2. The marking device of claim 1, wherein the furanone is fluorescamine.

3. The marking device of claim 1, wherein the solvent in the tube is ethanol.

4. The marking device of claim 1, wherein the housing is formed of flexible polyvinyl chloride.

5. The marking device of claim 1, wherein the tube is glass.

6. The marking device of claim 1, wherein the nib is formed of high density polyethylene.

7. The marking device of claim 1, wherein the furanone is fluorescamine; the solvent in the tube is ethanol; the housing is formed of flexible polyvinyl chloride; the tube is glass and the nib is formed of high density polyethylene.

* * * * *